United States Patent [19]

Engelhardt et al.

[11] Patent Number: 4,786,063
[45] Date of Patent: Nov. 22, 1988

[54] BONE VISE

[75] Inventors: John A. Engelhardt; Richard R. Tarr, both of Warsaw, Ind.

[73] Assignee: Boehringer Mannheim Corporation, Indianapolis, Ind.

[21] Appl. No.: 106,054

[22] Filed: Oct. 7, 1987

[51] Int. Cl.[4] .......................... B25B 5/04; B25B 5/08
[52] U.S. Cl. ...................... 279/106; 279/35; 269/237; 269/254 MW; 128/346
[58] Field of Search .................. 279/35, 38-40, 279/106; 128/92 VY, 92 VZ, 346; 269/237-239, 254 R, 254 MW

[56] References Cited

U.S. PATENT DOCUMENTS

| | | | |
|---|---|---|---|
| 871,962 | 11/1907 | Stewart | 51/273 |
| 925,212 | 6/1909 | McConville | 56/333 |
| 941,831 | 11/1909 | Widmann | 81/7 |
| 1,022,761 | 4/1912 | Stvanek | 279/106 |
| 1,307,011 | 6/1919 | Kohn | 279/106 |
| 1,467,508 | 9/1923 | Seng | 285/313 |
| 1,489,377 | 4/1924 | Wood et al. | 279/106 |
| 2,448,881 | 9/1948 | Glynn | 279/106 |
| 3,022,067 | 2/1962 | Stolz | 269/127 |
| 3,612,254 | 10/1971 | Wideman | 198/179 |
| 3,902,727 | 9/1975 | Banvas et al. | 279/106 |
| 3,952,384 | 4/1976 | Goldry et al. | 24/249 HA |
| 4,078,539 | 3/1978 | Sprague | 125/35 |
| 4,619,460 | 10/1986 | Rohm | 279/19 |

FOREIGN PATENT DOCUMENTS 660671  5/1979  U.S.S.R. ............... 128/92 VZ

Primary Examiner—John McQuade
Assistant Examiner—Steven C. Bishop
Attorney, Agent, or Firm—Perman & Green

[57] ABSTRACT

A bone vise for holding a bone or bone fragment immobile during surgery to enable a surgeon to perform desired sculpting or other operations thereon. The vise includes a planar base member with an integral threaded post upstanding from its central portion and a platform threadedly received on the post. A plurality of elongated gripper members are pivotally mounted intermediate their ends on the platform about axes which are tangent to a circle whose center lies within a bone receiving and engaging region. Each gripper member has a toothed surface at one end adjacent the bone receiving and engaging region and a cam surface at the opposite end weight biased into engagement with the base member. Rotation of the platform in one direction causes movement thereof away from the base member and enlargement of the bone receiving and holding region for insertion or removal of the bone. Rotation of the platform in the opposite direction causes movement thereof toward the base member and reduction of the bone receiving and holding region for gripping of the bone by the toothed surfaces of the gripping members. The base member may include a bearing surface with a low coefficient of friction for engagement by the cam surfaces. At least one handle member integral with the base member may be provided for lifting the base member and for maintaining the base member in a desired position.

15 Claims, 3 Drawing Sheets

BONE VISE

BACKGROUND OF THE INVENTION

I. Field of the Invention

The present invention relates to a bone vise for selectively receiving, gripping, and releasing a broad range of sizes of bones or bone fragments to be operated upon in the course of a surgical procedure.

II. Description of The Prior Art

Bone surgery has become ever more commonplace. It encompasses the complete replacement of a bone system or the relatively minor repair of a bone which is intended to remain in the patient. Diseased or accidentally fractured bones can now be repaired to enable a patient to recover to a state of use which would have been difficult to imagine just a few years ago. Such repair surgery includes autograft surgery according to which voids and defects in the bone of a patient are filled with other bone obtained from that individual. If the bone is obtained from another individual, it is referred to as allograft surgery. In either instance, the implanted bone acts as a lattice work for new bone ingrowth. Usually transplanted bone revascularizes, that is, it accepts and supports the growth of new blood vessels.

Up to the present time, there have been no known devices intended specifically for the support of a bone during a surgical procedure. Rather, it has been customary for nurses, operating room technicians, or assistants to hold a bone while the surgeon operated upon it. In some instances, they would hold the bone as best they could with their hands. In other instances, it was known to pass wires through one or more holes drilled in the bone, with the wires being held to stabilize the bone during the surgical procedure. However, these past efforts have not been satisfactory because the bone or bone fragment has not been held sufficiently steady to enable the precise sculpting or other operations needed to be performed by the surgeon. Additionally, manual holding of the bone was unsafe to the holders who are subject to unintended but ever possible cuts and abrasions by reason of the knives, drills and other cutting instruments used by the surgeon. This has become a major concern in light of the recent AIDS controversy.

While vise and chuck arrangements are widely known and used for a variety of other purposes, such known devices are not readily adaptable for firmly holding bones and bone fragments during a surgical procedure.

Typical of such known devices are U.S. Pat. Nos. 871,962, 925,212, 941,831, 1,022,761, 2,448,881, and 3,952,384. A known device having orthopedic application is disclosed in USSR No. 660,671 which is said to reposition and to place into compression bone fragments by means of a plurality of pivotally mounted levers. One end of each of the levers supports a thrust needle for insertion into a bone and the other end is captured at the periphery of a nut. As the nut is screwed on its mating shank, the thrust needles are moved relative to the bone fragments being operated upon.

Although the foregoing devices satisfied the goals for which they were each intended, none specifically addressed the problem of providing a device of simplified construction for firmly holding a bone or bone fragment outside the body during a surgical procedure and including the following features: solid, yet portable; rapidly opened to receive the bond and rapidly closed to firmly grip the bone; autoclavable; and easily operated.

SUMMARY OF THE INVENTION

The present invention was developed to fill the need for a bone holding instrument which would satisfy the needs which have just been described. To this end, a bone vise is disclosed for holding a bone or bone fragment immobile during surgery to enable a surgeon to perform desired sculpting or other operations thereon. The vise includes a planar base member with an integral threaded post upstanding from its central portion and a platform threadedly received on the post. A plurality of elongated gripper members are pivotally mounted intermediate their ends on the platform about axes which are tangent to a circle whose center lies within a bone receiving and engaging region. Each gripper member has a toothed surface at one end adjacent the bone receiving and engaging region and a cam surface at the opposite end weight biased into engagement with the base member. Rotation of the platform in one direction causes movement thereof away from the base member and enlargement of the bone receiving and holding region for insertion or removal of the bone. Rotation of the platform in the opposite direction causes movement thereof toward the base member and reduction of the bone receiving and holding region for gripping of the bone by the toothed surfaces of the gripping members.

The base member may include a bearing surface with a low coefficient of friction for engagement by the cam surfaces. At least one handle member integral with the base member may be provided for lifting the base member and for maintaining the base member in a desired position.

The present invention exhibits a number of beneficial features. In the first instance, it is of simplified construction, easily used, and easily cleaned following use. Additionally, the bone vise of the invention opens rapidly to receive a bone, and closes rapidly to its gripping position to render the bone immobile. Materials for construction of the bone vise are preferably chosen such that it is autoclavable. Furthermore, the bone vise of the invention can hold virtually the entire range of sizes of bone in the body of a human being from the largest which is approximately 58 mm across to the smallest which is approximately 3 mm across. Furthermore, the gripper members are undercut enabling them to hold irregularly shaped bones as well as regularly shaped bones.

Other and further features, advantages, and benefits of the invention will become apparent from the following description taken in conjunction with the following drawings. It is to be understood that the foregoing general description and the following detailed description are exemplary and explanatory but are not to be restrictive of the invention. The accompanying drawings, which are incorporated in and constitute a part of this invention, illustrate one of the embodiments of the invention, and, together with the description, serve to explain the principles of the invention in general terms. Like numerals refer to like parts throughout the disclosure.

DETAILED DESCRIPTION OF THE PREFERRED EMBODIMENT

Figure 1:
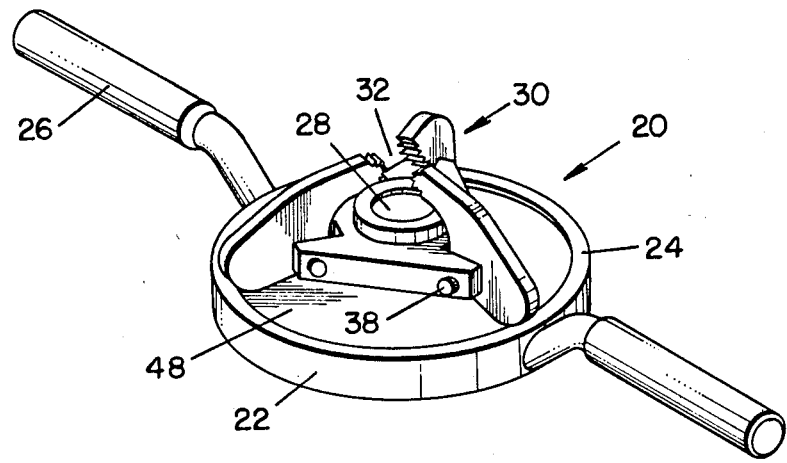
FIG. 1 is a perspective view of an assembled bone vise embodying the invention.
Figure 2:
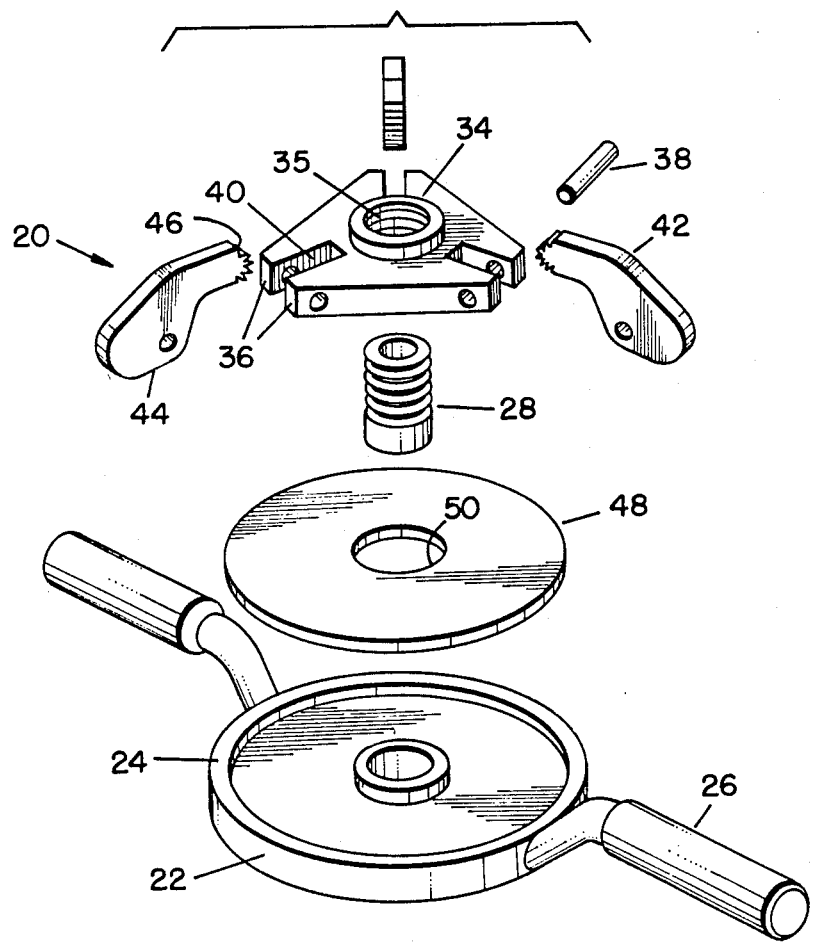
FIG. 2 is an exploded view of the bone vise illustrated in FIG. 1.
Figure 3:
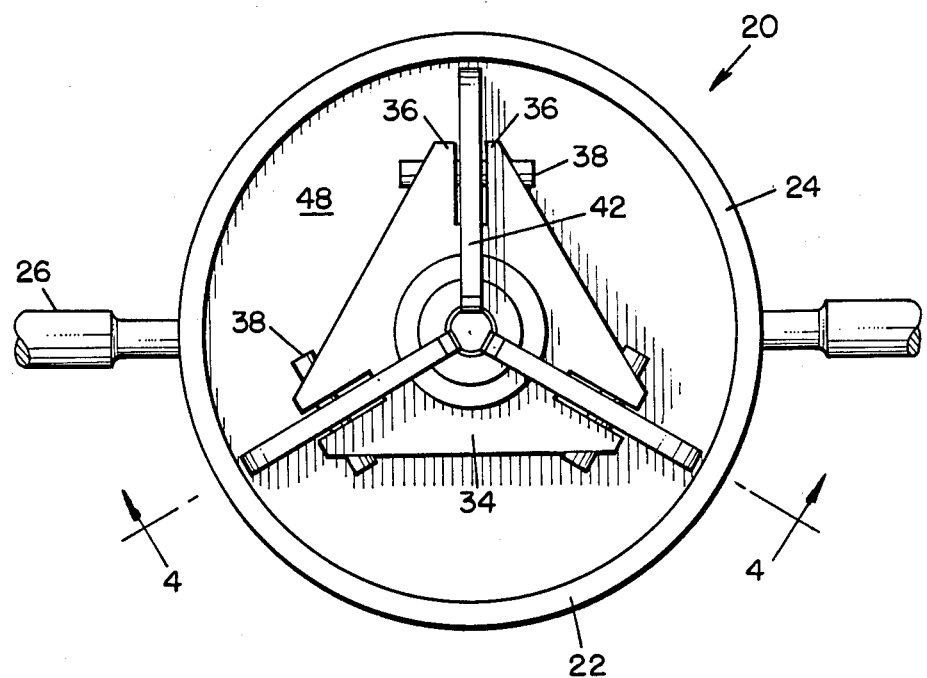
FIG. 3 is a top plan view of the bone vise.

Turn now to the drawings and initially to FIG. 1 which illustrates a bone vise 20 constructed in accordance with the invention. The bone vise includes a base member 22 which is illustrated as being circular and generally planar. Its outline is defined by an annular rim 24 and a pair of outwardly extending handles 26 may be provided for lifting the base member and maintaining the base member in a desired position. However, it will be appreciated that one or both of the handles 26 may be eliminated without adversely affecting the operation of the invention.

A threaded post 28 is integral with the base member 22, its lower end being fittingly received in a central bore 29, or otherwise joined thereto. The post 28 extends outwardly from the base member and, preferably, is perpendicular to the base member, extending from a center thereof.

Multiple jaw means 30 cooperate to define a bone receiving and gripping region 32 at locations disposed generally centrally of the annular rim 24.

Platform member 34 is generally triangular shaped with a central threaded bore 35 for engagement on the post 28. The platform member 34 is therefore generally parallel to the base member 22 and, upon rotation relative to the base member, moves either toward or away from the base member. At each of its apices, the platform member 34 is bifurcated to define spaced apart fingers 36 which are drilled crosswise to fittingly receive pins 38 which extend across a recess 40 between the fingers 36.

The jaw means 30 include three cooperating gripper members 42 which are elongated and have a cam surface 44 at one end and a toothed surface 46 at an opposite end proximate to the region 32. Each gripper member 42 is suitably pierced intermediate cam surface 44 and toothed surface 46 so as to freely receive an associated pivot pin 38. Thus, it will be appreciated that the gripper means 42 lie in planes which include the longitudinal axis of the threaded post 28 and extend in directions radially away from that axis. By way of further definition, the pivot pins 38 are equally distant from the axis of the post 28 and are all tangent to a circle whose center is the axis of the post 28, which axis lies within the bone receiving holding region 32.

A disk-shaped bearing 48 has a central aperture 50 for reception over the post 28 and is sized and shaped to conform to the annular rim 24. The bearing 48 rests on the upper surface of the base member 22, has a substantially planar surface and merely rests on the base member, thereby allowing it to spin freely relative to the base member. This construction enables ready replacement of the bearing should it wear out and also allows it to be removed easily for cleaning. The bearing 48 is preferably composed of "DELRIN" brand or equivalent, moderately hard plastic material which has a low coefficient of friction. The fingers 36 are biased so that the cam surfaces engage the bearing surface 48. It is preferable that this bias be achieved by appropriately weighting the gripper members 42, although it is possible for an appropriately placed and sized spring to perform this function. However, it is preferred that springs not be employed since they add an additional component to the bone vise thereby increasing its cost and complexity and tend to collect residue which should be cleaned off between uses. Such residue, if permitted to build, would not only be unsanitary, but can also adversely effect the operation of the bone vise 20.

Figure 4:
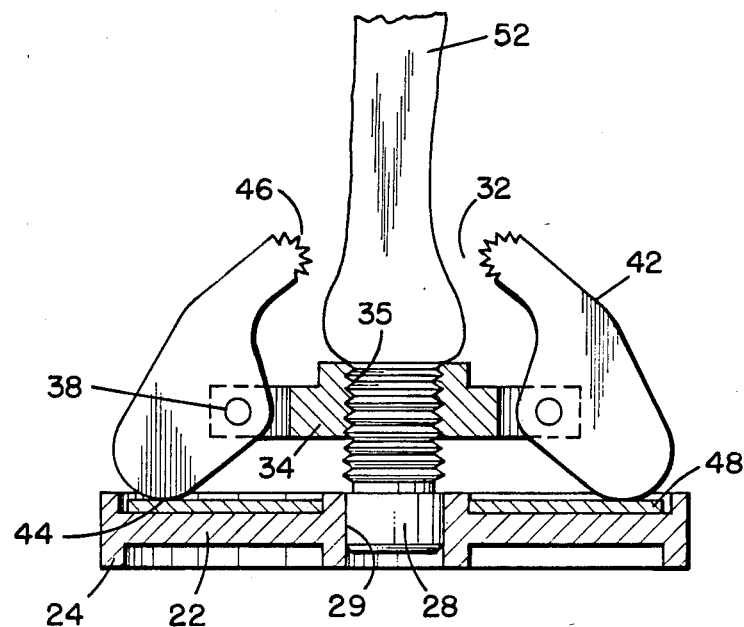
FIG. 4 is a cross section view taken generally along line 4—4 in FIG. 3 illustrating the bone vise in an open, bone receiving position.
Figure 5:
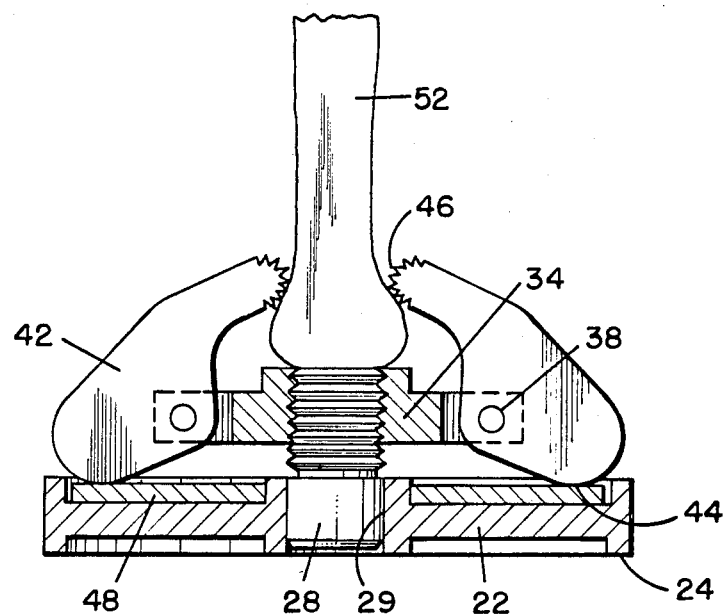
FIG. 5 is a cross section view, similar to FIG. 4, illustrating the bone vise in a bone engaging position.

Thus, when the bone vise 20 assumes the normal upright position as illustrated in FIG. 1, it will be appreciated that the gripper members 42 are biased to the open position (FIG. 4). That is, the gripper members 42 pivot on the pins 38 until the cam surfaces 44 engage the surface of the bearing 48. Depending upon the hand of the threaded post 28, the surgeon rotates the platform member 34 in one direction which causes movement of the platform member away from the base member 22 and toward a first position (FIG. 4) adapted to receive or release a bone or bone fragment 52. In a similar, but opposite, manner, rotation of the platform member 34 in the opposite direction causes movement of the platform toward the base member 22 and, simultaneously, of the gripper members 42 toward the second, bone engaging position (FIG. 5). The pitch of the threads of the post 28 are chosen to assure that there is a proper relationship between the amount of rotation of the platform member 34 to achieve an accompanying movement of the gripper members 42. Also, the mating threads on the post 28 and platform member 34 are preferably designed to prevent unintended loosening of the gripper members once they have reached the bone engaging position.

It should be understood that the invention is not limited to the particular embodiment shown and described herein; indeed, various changes and modifications may be made without departing from the spirit and scope of this novel concept as defined by the following claims.

We claim:

1. A bone vise for releasably holding a bone to be operated upon comprising:

a base member having a substantially planar bearing surface;

platform means being a unitary member adapted to supportively receive a bone thereon to be operated upon mounted for selective movement toward and away from said bearing surface; and jaw means pivotally mounted on said platform means and freely engageable with said bearing surface, said jaw means movable between a first position for freely receiving the bone to be operated upon when said platform means is distant from said base member and a second position for firmly gripping the bone and preventing relative movement between the bone and said base member when said platform means is proximate to said base member.

2. A bone vise as set forth in claim 1 wherein said jaw means include:

at least three elongated gripper members, each having a cam surface at one end engageable with said bearing surface, a toothed surface at an opposite end, and being pivotally mounted on said platform means intermediate said cam surface and said toothed surface.

3. A bone vise as set forth in claim 2 wherein said platform means includes a plate lying generally in a plane parallel to said base member; and wherein said toothed surfaces of said gripper members define a centrally located bone receiving and holding region, said gripper members being pivotally mounted about axes which are tangent to a circle whose center lies within said bone receiving and holding region.

4. A bone vise as set forth in claim 3 wherein said cam surfaces are biased into engagement with said base member.

5. A bone vise as set forth in claim 4 wherein said base member is substantially planar and includes:
a bearing member mounted thereon having said substantially planar bearing surface thereon with a low coefficient of friction, said bearing surface lying in a plane substantially perpendicular to the directions of movement of said platform means toward and away from said biasing surface.

6. A bone vise as set forth in claim 5 wherein sadi bearing member is composed of a moderately hard plastic material.

7. A bone vise as set forth in claim 1 including:
at least one handle member integral with said base member for lifting said base member and for maintaining said base member in a desired position.

8. A bone vise as set forth in claim 2 wherein said jaw means include:
at least three elongated gripper members, each having a cam surface at one end engageable with said bearing surface and a toothed surface at an opposite end; and
means pivotally mounting each of said gripper members intermediate said cam surface and said toothed surface, said gripper membes being biased such that said cam surfaces engage said bearing surface.

9. A bone vise comprising:
a base member having a substantially planar bearing surface;
a threaded post upstanding from said base member:
multiple jaw means for releasably receiving and gripping a bone intended to be operated upon, said jaw means including cooperating gripper members defining a centrally located bone receiving and holding region, said gripper members being movable between a first position for freely receiving the bone and a second bone gripping position; and
including a platform member being a unitary member adapted to supportively receive a bone thereon to be operated upon threadedly engaged with said post whereby rotation of said platform member in one direction causes movement of said platform member away from said bearing surface and movement of said gripper members toward said first position and whereby rotation in the opposite direction causes movement of said platform member toward said bearing surface and movement of said gripper members toward said second position at which relative movement between the bone and said platform member is prevented.

10. A bone vise as set forth in claim 9 including:
at leat three of said gripper members;
each of said gripper members being elongated and having a cam surface at one end thereof freely engageable with said base member, a toothed surface at an opposite end, and being pivotally mounted on said platform member intermediate said cam surface and said toothed surface.

11. A bone vise as set forth in claim 10 wherein said platform member lies generally in a plane parallel to said bearing surface; and
wherein said gripper members are pivotally mounted about axes which are tangent to a circle whose center lies within said bone receiving and holding region.

12. A bone vise as set forth in claim 11 wherein said gripper members are weighted such that when said bone vise is so oriented that said base member is positioned beneath said holder plate, said cam surfaces are caused to engage said bearing surface.

13. A bone vise as set forth in claim 12 wherein said base member is substantially planar and includes:
a bearing member mounted thereon having said substantially planar bearing surface thereon with a low coefficient of friction, said bearing surface lying in a plane substantially perpendicular to the directions of movement of said platform means toward and away from said biasing surface.

14. A bone vise as set forth in claim 13 wherein said bearing member is composed of a moderately hard plastic material.

15. A bone vise as set forth in claim 9 including:
at least one handle member integral with said base member for lifting said base member and for maintaining said base member in a desired position.

* * * * *